United States Patent
Janssen et al.

(10) Patent No.: US 9,980,688 B2
(45) Date of Patent: May 29, 2018

(54) CEILING SUSPENSION SYSTEM

(71) Applicant: KONINKLIJKE PHILIPS N.V., Eindhoven (NL)

(72) Inventors: Erik Johannes Maria Janssen, Eindhoven (NL); Johannes Herman Hubertus Mathijs Van Garderen, Best (NL); Johan Juliana Dries, Arendonk (BE); Arnoldus Johannes Maria Van Der Stappen, Nuenen (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days. days.

(21) Appl. No.: 14/655,956

(22) PCT Filed: Jan. 16, 2014

(86) PCT No.: PCT/EP2014/050744
§ 371 (c)(1),
(2) Date: Jun. 26, 2015

(87) PCT Pub. No.: WO2014/111437
PCT Pub. Date: Jul. 24, 2014

(65) Prior Publication Data
US 2015/0342547 A1 Dec. 3, 2015

(30) Foreign Application Priority Data
Jan. 17, 2013 (EP) ..................... 13151572

(51) Int. Cl.
*A61B 6/00* (2006.01)
(52) U.S. Cl.
CPC .......... *A61B 6/4441* (2013.01); *A61B 6/4464* (2013.01); *A61B 6/4423* (2013.01)
(58) Field of Classification Search
CPC ............ A61B 6/4441; A61B 6/4464
See application file for complete search history.

(56) References Cited

U.S. PATENT DOCUMENTS 5,050,204 A    9/1991  Siczek et al.
5,410,584 A *  4/1995  Schaefer .............. A61B 6/4441
                                           378/196
(Continued)

FOREIGN PATENT DOCUMENTS

CN    1161190 A    10/1997
JP    2001029337 A   2/2001
(Continued)

OTHER PUBLICATIONS

"Advanced interventions in your lab", Philips Allura Xper FD20 system specifications. 2009 Koninklijke Philips Electronics N.V. Netherlands.
(Continued)

*Primary Examiner* — Eliza Osenbaugh-Stewart

(57) ABSTRACT

The present invention relates to acquisition of medical image information of an object. In order to improve operating theaters and allow more effective use of equipment and staff during interventions, a medical X-ray system (10) is provided, comprising a patient support (12), an X-ray image acquisition arrangement (14), a support arrangement (16), and a rail arrangement (18). The image acquisition arrangement (14) acquires imaging information of an object of interest (20) arranged on the patient support (12). The rail arrangement (18) is provided overhead. The support arrangement (16) is movably mounted to the rail arrangement (18), and at least movable along the rail arrangement (18). The image acquisition arrangement (14) is movably mounted to the support arrangement (16) to allow image acquisition of the object (20) from different directions. The rail arrangement (18) is arranged transversely to a longitudinal direction of the patient support.

10 Claims, 4 Drawing Sheets

(56) References Cited

U.S. PATENT DOCUMENTS

| | | |
|---|---|---|
| 5,740,227 A | 4/1998 | Kusch |
| 6,264,364 B1 | 7/2001 | Pflaum et al. |
| 7,018,097 B2 | 3/2006 | Schmitt |
| 7,220,052 B2 | 5/2007 | Gotoh |
| 7,246,943 B2 | 7/2007 | Gotoh |
| 7,594,751 B2 | 9/2009 | Grebner et al. |
| 8,047,715 B2 | 11/2011 | Noordhock |
| 8,542,160 B2 | 9/2013 | Sakaniwa |
| 8,591,107 B2 | 11/2013 | Peters |
| 8,872,313 B2 | 10/2014 | Ushio et al. |
| 2001/0005410 A1* | 6/2001 | Rasche .............. A61B 6/4441 378/197 |
| 2002/0118793 A1* | 8/2002 | Horbaschek ........ A61B 6/4233 378/197 |
| 2003/0112926 A1 | 6/2003 | Atzinger |
| 2003/0233040 A1* | 12/2003 | Sakaniwa .......... A61B 6/4464 600/407 |
| 2004/0008820 A1* | 1/2004 | Schmitt .............. A61B 6/4441 378/193 |
| 2005/0195945 A1 | 9/2005 | Gotoh |
| 2009/0074151 A1 | 3/2009 | Henderson et al. |
| 2010/0082147 A1 | 4/2010 | Damvig et al. |
| 2011/0268254 A1* | 11/2011 | Peters ................. A61B 6/4441 378/197 |
| 2012/0074543 A1 | 3/2012 | Akira et al. |
| 2014/0022353 A1 | 1/2014 | Hamersma et al. |
| 2015/0342547 A1 | 12/2015 | Janssen et al. |

FOREIGN PATENT DOCUMENTS

| | | |
|---|---|---|
| JP | 2003289475 A | 10/2003 |
| JP | 2002306461 A | 5/2004 |
| JP | 2012239633 A | 12/2012 |
| WO | 2009110906 A1 | 9/2009 |

OTHER PUBLICATIONS

"Artis zee, Ceiling-mounted system for surgical angiography VC 14" Data sheet. 2009. 222.siemens.com/healthcare.Germany.

* cited by examiner

CEILING SUSPENSION SYSTEM

CROSS-REFERENCE TO PRIOR APPLICATIONS

This application is the U.S. National Phase application under 35 U.S.C. § 371 of International Application Serial No. PCT/EP2014/050744, filed on Jan. 16, 2014, which claims the benefit of EP Application Serial No. 13151572.8, filed on Jan. 17, 2013. These applications are hereby incorporated by reference herein.

FIELD OF THE INVENTION

The present invention relates to acquisition of medical image information of an object. In particular, the present invention relates to a medical X-ray imaging system for providing medical imaging information of an object.

BACKGROUND OF THE INVENTION

X-ray interventions become more and more complex, in particular due to the required systems and devices, as well as staff and third party equipment. In particular, fixed X-ray systems are often used in operating theatres to enable minimally invasive or mixed procedures. With the evolution of methods and available technologies, such operating theatres comprise an increasing number of equipment and medical staff. An effective cooperation of involved equipment and staff can be become important for effective interventions. WO 2010/137116 A1 describes a safety system for a dynamic 3D health care environment and a medical examination system with motorized equipment.

SUMMARY OF THE INVENTION

Hence, there may be a need to improve operating theatres in order to allow a more effective use of equipment and staff during interventions.

The object of the present invention is solved by the subject-matter of the independent claims, wherein further embodiments are incorporated in the dependent claims.

According to the invention, a medical X-ray imaging system is provided, which comprises a patient support, an X-ray image acquisition arrangement, a support arrangement, and a rail arrangement. The image acquisition arrangement acquires image information of an object arranged on the patient support. The rail arrangement is provided overhead, and the support arrangement is movably mounted to the rail arrangement. The support arrangement is movable at least along the rail arrangement. The image acquisition arrangement is movably mounted to the support arrangement to allow image acquisition of the object from different directions. Further, the patient support has a longitudinal direction, and the rail arrangement extends in a longitudinal rail direction transversely to the longitudinal direction of the patient support.

An advantage of transversely arranged rails can be seen in a possibility to move the imaging system, in particular the X-ray image acquisition arrangement, out of an activity area, for instance out of the space, that is needed for the medical staff to stand and move. Transversely arranged rail arrangements are furthermore advantageous, if room areas on the lateral side of the patient support can be used. Due to the possibility to transversely move the image acquisition arrangement in relation to the patient, off-centre imaging can be conducted.

The rail arrangement can comprise a longitudinal extension, which can, for instance, be in the range of a length of the patient support. This allows a necessary degree of mobility of the image acquisition arrangement and at least a part of the support arrangement. For instance, such a transversely extending rail arrangement can extend from one sidewall to another opposing sidewall to allow the image acquisition system to be moved completely outside of the patient support area or out of a centre of an operating theatre to park the image acquisition system, for example, in a side area of a room. A possibility to move equipment out of a patient treatment area can be very important for preparation or cleaning of the operating theatre and preparation of a patient before and after an intervention. In addition, sterility and hygienic aspects can be better considered. In other words, a transversely arranged rail arrangement allows an X-ray image acquisition arrangement to be positioned around the patient to acquire images, but also provides favourable stand-by positions, when equipment is not actively needed. In addition, a parking position can be possible, wherein imaging equipment can be completely moved out of way and out of an active zone of an operating theatre.

In general, the rail arrangement is preferably adapted to carry or suspend large and heavy components, such as X-ray imaging systems, that need mechanically stable suspension. However, also any other imaging technologies or medical equipment, that require precise positioning and stable suspension, can be used in conjunction with the described arrangement of rails and support.

The rail arrangement can thereby be positioned anywhere in a room, for instance at the ceiling. More specifically, it can further be installed in an area vertically above the patient support, but also vertically outside or besides the patient support.

The term "imaging" relates to a method, wherein X-ray is generated with an X-ray source, subsequently an object is irradiated by X-ray radiation, and a detector receives or detects the portion of radiation which has passed the object of interest. The detector generates data, which represents the detected radiation. The data can then be used to generate or construct an image of the object of interest.

The term "imaging information" is related to data representing tissue structure with different absorption behaviour in terms of X-ray radiation. Such data are depending on the detector technology and kind of radiation used.

A patient support can be seen as a table or other mostly mechanical means for supporting a patient or object. One objective of a patient support can be to prevent movement of the object in order to avoid problems during imaging or during the intervention. Typically, the patient support can be arranged horizontally, however, tilting and/or rotation can be possible. Also lateral and longitudinal movements can be possible.

A region of interest of an object, for instance a patient's body, is arranged on the patient support. The X-ray source and the detector can be positioned at an upper and a lower side or sideward of the table, to allow a precise image acquisition.

An image acquisition arrangement can include, for example, a C-arc, which holds or supports an X-ray source, X-ray detector, and allows correct arrangement of the X-ray components for imaging.

The term "rail arrangement" means that one or more rails, typically in parallel, are arranged to allow a movement of a connected part or member along the rails. The rail arrangement can be preferably fixed to a ceiling, side walls or other immobile members of an operation theatre in order to provide a stabilizing effect. The rail arrangement can be, for example, a wheel-rail combination, sleeve bearing or other means moving on or along the rails. An objective of such a rail arrangement can be to minimize forces between the support arrangement and the rail arrangement to allow low friction and therefore low forces for initiation of movements. Furthermore, fixation can be possible to prevent unwanted movement. A fixation can ensure that the image acquisition arrangement does not move, for instance, during an image acquisition procedure. If the position of the image acquisition arrangement is desired to be changed, it can be possible, to release the fixation and slide or move the image acquisition arrangement and the support arrangement along the rails. When arrived at the destination position at the rail arrangement, the support system can then be fixed or arrested again. In one example, the rail arrangement is mounted to the ceiling, preferably using two rails in parallel for distribution of forces. A distance between two rails for suspension of an X-ray imaging system can, for instance, be in the range of 20 cm to 100 cm.

The term "overhead" can be understood that the rail system is located in a vertical height above ground over the heads of medical staff approximately, for example, at least 2 meters over ground, to avoid collision of imaging system components with staff or with other equipment.

In another example, rails are mounted with their ends to the sidewalls of the room spanning across the room. An advantage can be seen in a use of such rail arrangement in rooms with very high ceilings or not sufficiently stable ceiling structures, which do not allow mounting of heavy equipment.

In another example, rails are mounted on a bridge-like arrangement with stands on the floor. This can be advantageous, if no sufficiently stable ceiling or stable/rigid side walls are available.

The support arrangement allows a stable positioning of the image acquisition arrangement by providing a mechanical link to the immobile rail arrangement. Stability can be achieved by a move-and-lock functionality. Preferably, the support arrangement is adapted to allow a manual moving by medical staff, or, alternatively, allows to be moved through motor arrangements. Such motors or drives can be provided, for example, at connection points between the support arrangement and the image acquisition arrangement and/or the rail arrangement. The support arrangement can preferably be designed to be at least partly located in a minimum vertical height over the heads of medical staff or equipment to minimize blocking of space and avoid collisions.

In one example, the support arrangement comprises segmented arms, which are connected with hinges. In another example, the support arrangement comprises telescopic arms, which can be driven, for instance, hydraulically or electromagnetically with drives and gear mechanism. It should be noted, that telescopic arms are seen as having at least two structural members or segments.

A moving along the rail arrangement can be seen as a translation movement by shifting or sliding of the support arrangement on or at the rails. This translation can be combined with a possible pivoting movement or rotation of the support arrangement around a mounting point of the support arrangement at the rail arrangement.

The term "movably mounted" refers to a possibility to change a position while staying physically connected, and the capability to provide a necessary stability and a temporary fixation to allow the acquisition of images using the image acquisition arrangement. A movable mounting of the image acquisition arrangement to the support arrangement refers to a capability of the image acquisition arrangement to allow different projection directions. For example, rotation of an image acquisition system around an iso-point is often desirable. In other words, a movement of the image acquisition arrangement in 3D space can be advantageous.

A longitudinal patient support direction relates to the main geometric extension. According to the shape of a human body, a patient support for a human body typically comprises a bigger longitudinal extension (e.g. head-feet-axis of a patient) than a lateral extension. For example, a patient support can have a size of about 2 to 3 meters length and about 50 cm to 80 cm width. If the table is tilted or rotated, the horizontal direction relates to a projected direction of the patient support in horizontal direction.

The term "transversely" relates to an angular relation between two members that is not parallel. In other words, it is related to directions, which allow a lateral movement related to a longitudinal extension of the patient support. Hereby, a preferred arrangement can be an orthogonal arrangement with a deviation of +/−30 degrees, or with +/−20 degrees, or with +/−15 degrees, or with +/−10 degrees or with +/−5 degrees.

According to an example, the rail arrangement is disposed above and besides the patient support also includes vectors with a horizontal component.

An advantage can be seen in an avoidance of blocking of an operational area around the table, where usually staff is moving and working. Furthermore, collision with other equipment can be avoided.

The term "besides" refers to a positioning of the rail arrangement horizontally next to or away from the patient table or patient support.

The term "above" means that the rail arrangement is positioned vertically higher over the ground than the patient support. For example, the rail arrangement can be mounted at the ceiling or at sidewalls with mounting points vertically higher than the patient support. In other words, an arrangement of the rail arrangement above and besides the patient support aims to remove rails from an area, where staff is working or where other equipment is positioned for patient treatment.

According to an example, the patient support is at least partly surrounded by a predetermined patient access zone. The rail arrangement is further disposed above and outside of the patient access zone.

A patient access zone can be seen as the patient support surrounded by a margin around the patient support. In other words, an arrangement of the rail arrangement outside of the patient access zone is aimed to avoid collisions or interference of any parts of an imaging system with staff or other equipment.

Another advantage can be seen in an unblocked access to the patient for staff and important equipment. Furthermore, improved footprint, more space for moving, and access to the head region of a patient can be achieved. The head region of a patient can be important for providing space for anaesthetists, which are usually located near the head region of patient.

According to an example, the patient support is at least partly located in a predetermined laminar flow zone. The rail arrangement is disposed outside the laminar flow zone.

An advantage can be seen in the fact that the rail arrangement does not disturb or negatively affect the laminar flow. A laminar flow relates to a parallel air stream with no or minimal turbulences, supporting sterility in an operating theatre, in particular in the area of the patient support. A laminar flow is usually vertical, downwardly oriented, and therefore often described as "down-flow". Due to the required parallel streams and the objective to avoid turbulences, it is desired to keep objects out of the laminar flow zone. Any object in the laminar flow zone can generate turbulences and can introduce germs and can lower sterility. The air provided in the laminar flow zone can be pre-treated and filtered to ensure sterility.

In one example, the laminar flow zone covers exactly the patient support zone. However, it can also cover a larger zone or only parts of the patient support. Thus, in one example, the laminar flow zone only covers the area, where the intervention takes place, which can be smaller than the whole patient table or patient support.

In one example, an outlet arrangement of an air supply system is arranged vertically below the rail arrangement, and rails extend transversely to the patient support or patient table.

In this case, the rail arrangement can be disposed vertically above the patient support. For example, the support arrangement can be adapted to horizontally bypass the air outlet arrangement.

According to an example, the support arrangement is adapted to position the image acquisition arrangement at least:

in an operational position, in which the image acquisition arrangement acquires image information of the object of interest; and in a parking position, in which the image acquisition arrangement is provided outside the patient access zone and/or outside the laminar flow zone.

An advantage can be that the imaging system provides different spatial positions for different situations during the invention. An advantage of a parking position can be seen in the possibility to move the heavy and large imaging system completely out of any area, where space is needed during interventions or for staff and equipment to move. In particular for room preparation, patient preparation, cleaning or maintenance, a parking position provides spatial advantages.

An operational position of the image acquisition arrangement allows acquiring imaging information of the object from multiple different projection angles and positions. An X-ray source and an X-ray detector can be activated normally only when the image acquisition arrangement is in operational mode. In other words, the parking position is aimed to minimize any disturbing influence, in particular minimize space required. In an example, the imaging system can be parked parallel to a sidewall. The imaging system can be, if necessary, maintained in that parking position, if necessary.

According to an example, the support arrangement allows the image acquisition arrangement to be positioned in a stand-by position, in which the image acquisition arrangement is outside of the patient access zone. An advantage can be seen in an advantageous ratio of quick availability for a required image acquisition, and in the necessity to avoid or at least minimize any interference with imaging equipment and the laminar flow. In an example, a stand-by position can be between an operational position and a parking position, and be located outside of a predetermined margin around a region of interest of the object on the patient support. Such a margin can be in a range of 0.5 meters to 2 meters, for instance.

According to an example, the support arrangement comprises a rail connector, at least two support arms, and an image acquisition connector. The rail connector couples the support arrangement to the rail arrangement. The image acquisition connector couples the image acquisition arrangement to the support arrangement. The support arms are movably connected to each other linking the image acquisition connector to the rail connector. An advantage of such an arrangement is a better mechanical stability and a better positioning of the image acquisition arrangement in a three-dimensional room. A rail connector can be seen as member, which allows movement along rails and provides stable coupling of support arrangement to rails.

For example, the rail connector can be implemented as a carriage, which is slideable or displaceable along a longitudinal direction of the rail arrangement. The image acquisition connector can allow an angle conversion between different pivotal axes. It further allows different movement options in different direction and dimensions without movement of support arms.

Support arms can be seen as providing bridging of distances in the three-dimensional room, while maintaining mechanical stability. The support arms can be adapted to carry the weight of image acquisition arrangement. In an example, support arms are light weight but mechanically stable. For instance, aluminium profiles, steel profiles, tube-like profiles, or similar material can be used to provide required mechanical properties of the support arms. The at least two support arms can be connected via hinges, bearings, or others. Furthermore, in another example, the support arms can be implemented as telescopic arm arrangement.

The term "movably connected" refers to the ability of the linked members to perform movements in different directions, while staying mechanically connected. In an example, the spatial position of connected members can be changed and fixed/arrested/locked. This allows the members to be moved in relation to each other and then be locked or arrested to avoid unwanted movement, for instance for image acquisition.

According to an example, a first horizontal support arm is mounted to the rail connector pivotally around a first downwardly oriented axis. A second vertical support arm is mounted to the first arm pivotally around a second downwardly oriented axis at a first end. The image acquisition connector is mounted to the second support arm at a second end, wherein the image acquisition arrangement is movable in relation to the second arm.

An advantage can be seen that the horizontal extension is provided above the heads of staff and does not disturb operation and does not block space. The horizontal extension is very effective to bridge horizontal distances between rails and the patient support area. The image acquisition connector and the rail connector provide pivotable mounting, and therefore additional degree of freedom for movement in multiple directions. In an example, the joint of the connector to the second arm provides the movement. In another example, a combination is provided of movement of arms and connectors. In an example, the first downwardly oriented axis is a first vertical axis. In another example, the second downwardly oriented axis is a vertical axis.

The term "horizontal" relates to a horizontal arrangement with possible deviations of plus 30 degrees to minus 30 degrees, for example +/−30 degrees, +/−20 degrees, +/−15 degrees, +/−10 degrees or +/−5 degrees. In other words, a horizontal extension can be combined with a vertical extension at the same time.

According to an example, the first support arm is mounted to the rail connector at a first mounting point, and the second support arm is mounted to the first support arm at a second mounting point. A horizontal distance between the first mounting point and the second mounting point is adjustable. In other words, a length of the first support arm is extensible in horizontal direction in order to allow a movement of the image acquisition arrangement along a longitudinal extension of the patient support.

An advantage can be seen in the extensibility, which provides a higher degree of mobility by effectively bridging a horizontal distance and allows an extended mobility in a direction longitudinal to the patient support and away from the rail arrangement. Another advantage can be that the image acquisition arrangement can perform a movement transversally in lateral direction, e.g. orthogonal, to the longitudinal direction of the patient support without changing an angle between the image acquisition arrangement and the patient support.

In one example, for the adjustment of the distance, at least one out of the group of the following is provided: translation of second mounting point along the first support arm; translation of first mounting point along the first support arm; and the first support arm is a telescopic arm.

In another example, the support arm arrangement consists of extensible arms, for instance, thread rod and rails. In one example, the members are driven by hydraulic means. In one example, the mounting point of second vertical arm is mounted slideable at the horizontal arm, for instance with multiple slideable rails.

According to an example, the image acquisition arrangement comprises a C-arm. An X-ray source and an X-ray detector are provided at opposing ends of the C-arm, wherein the C-arm is movably mounted to the image acquisition connector. The mounting of the C-arm is provided: sidewise at an intermediate portion midway between the opposing ends of the C-arm, wherein the image acquisition connector provides a pivoting movement of the C-arm around a horizontal axis (the "propeller movement"); or on top at the upper end of the two opposing ends, wherein the image acquisition connector provides a pivoting movement of the C-arm around a vertical axis.

An advantage can be seen in the fact that a C-Arm is an advantageous mechanical solution, which allows positioning an object of interest inside a C-shape, wherein the X-ray source and detector arrangement can be positioned to irradiate the object. Any mechanical contact is avoided between the patient support/object of interest and the image acquisition system.

In an example, when the image acquisition connector is arranged on the top or upper point of the C-arm, additionally a pivoting movement around a horizontal axis is provided. The image acquisition connector may be provided as a sliding guide device to allow angular variations of the source/detector axis. The support arrangement or image acquisition connector can also be connected at the lower or bottom side of the C-arc. The image acquisition connector can provide a pivoting of the C-arm around a vertical axis. The C-arm in conjunction with the image acquisition connector can also perform a rotation of the X-ray source/detector arrangement around an axis defined by the shape of the C-arc (C-arc rotation).

According to an example, the imaging system further comprises an air supply arrangement providing treated supply-air. Supply-air outlets are provided overhead supplying the supply-air in a laminar air-flow manner towards the patient support, defining a laminar flow zone.

As an advantage it can be seen that the air supply arrangement and the related laminar flow provide sterility and clean-room-like conditions to a specific area on at least a part of the patient support to minimize negative implications due to unsterile conditions. For example, such air supply arrangements are disposed such that no or minimal equipment or, for instance, heads of doctors/staff get into the air-flow or down-flow. For example, supply-air outlets can be located at or in the ceiling of an operation theatre. In another example, it is possible to dispose air outlets underneath other systems or mechanical elements, such that a free airflow from top down to the patient support is possible. An air supply arrangement can be understood as an arrangement of air outlets that generate an air flow, e.g. a laminar air-flow in the sense of non-turbulent parallel air-flows. In another example, air supply outlets are controlled in terms of the area which needs laminar flow. In other words, the arrangement of air outlets can be displaced or moved, depending on the area of intervention.

According to an example, the imaging system further comprises at least movable lighting equipment, movable display equipment, and/or media racks. The lighting equipment and/or display equipment and/or media rack are mounted overhead outside the laminar air zone.

An advantage of the further equipment items can be to provide staff with further improved working conditions. In particular, a distance can be minimized between operating staff and required equipment. This can lead to improved visibility and improved information accessibility to provide more effective interventions.

In another example, the movable lighting equipment or movable display equipment or media rack are disposed outside the patient access zone, outside the patient support, or a combination of both. In general, the aim is to minimize a risk of collision of an equipment and/or staff. For example, lighting equipment, display equipment, media racks, and others can be mounted using a suspension at the ceiling, which is achieved with a further or second orthogonal or transversal rail system at an opposing end of the patient support. This provides furthermore a possibility to move such equipment completely out of way, if not needed. The term "media rack" refers to a supply unit for further media and extended functions.

It can be seen as an idea of the invention to dispose or arrange the rail arrangement, which carries the image acquisition arrangement and the support arrangement, transversely to a longitudinal direction of a patient support.

BRIEF DESCRIPTION OF THE DRAWINGS

Exemplary embodiments of the invention will be described in the following with reference to the following drawings.

DETAILED DESCRIPTION OF EMBODIMENTS

Figure 1:
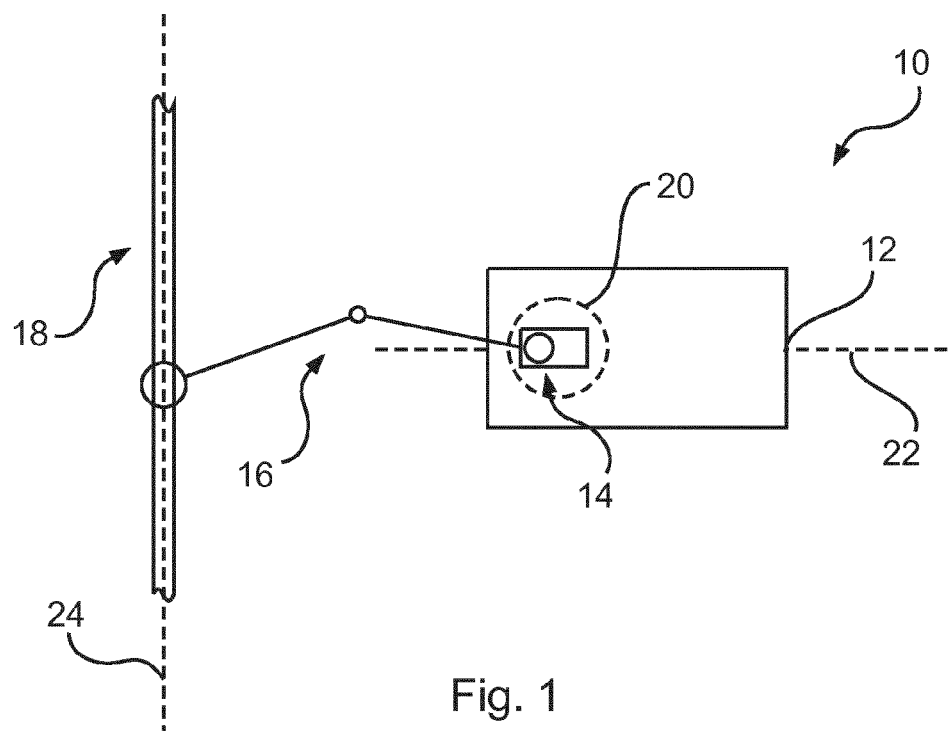
FIG. 1 schematically illustrates an example of a medical X-ray imaging system from a top view.

FIG. 1 describes a medical imaging system 10 based on X-ray for generation of imaging information of an object 20. The medical imaging system 10 comprises a patient support 12, which has a longitudinal horizontal extension or direction 22. A rail arrangement 18 has a longitudinal rail direction 24 and is mounted to a support arrangement 16. The support arrangement 16 is movably connected to the image acquisition arrangement 14. The rail arrangement 18 is transversely, or as shown in FIG. 1, orthogonally arranged in relation to the longitudinal extension 22 of the patient support 12.

The rail arrangement 18 can comprise one or several distinct rails which can be arranged such that a moving of the support arrangement 16 along the rails is possible. Instead of an exact orthogonal arrangement of the rail arrangement 18, also all other angles except a parallel arrangement related to the longitudinal extension 22 of the patient support 12 are possible. The rail arrangement 18 can also extend vertically above the patient support 12. The image acquisition arrangement 14 is movably connected, for instance with a hinge, to the support arrangement 16. The image acquisition arrangement 14 can acquire image information of an object of interest 20, which is positioned on a patient support 12. Due to the mobility in relation to the support arrangement 16, the image acquisition arrangement 14 can move in longitudinal and lateral direction in relation to the object 20. Preferably, the rail arrangement 18, the support arrangement 16, and the image acquisition arrangement 14 comprise dimensions and sizing, that allows positioning of the image acquisition system, in particular an X-ray source and an X-ray detector in all relevant areas of the patient support and/or the object of interest. The support arrangement 16 can comprise one or multiple segments or members to allow a moving of the image acquisition arrangement 14 in multiple directions. The support arrangement 16 is at least movable along the rail arrangement 18. In addition, for instance, a pivoting in several directions can possible.

Figure 2:
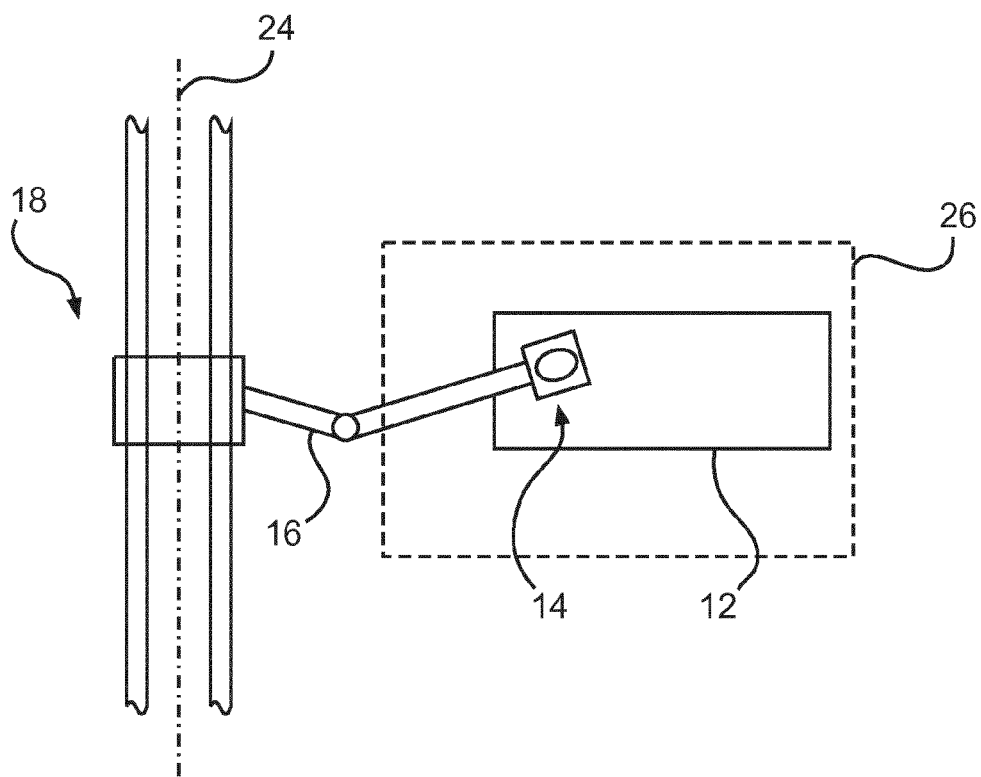
FIG. 2 schematically illustrates a medical X-ray imaging system from a top view with a patient access zone according to another example.

FIG. 2 describes an arrangement of rails 18, which consists of two parallel rails, having a longitudinal direction 24. The support arrangement 16 is connected to both of the rails 18, and movably connected to the image acquisition arrangement 14. Around a patient support 12, a patient access zone 26 is shown. The patient access zone 26 can be seen as an area around at least a part of the patient support 12, which is used for equipment and by medical staff to access the patient for treatment/interventions. The purpose of the patient access zone 26 can be seen that this zone is critical for effective interventions in the sense that sufficient space for moving for the staff is required, as well as space for medical equipment necessary. The patient access zone can cover the whole patient support 12 or only parts of the patient support 12. Although the FIG. 2 shows a rectangular shape, also other shapes are possible. An aspect of FIG. 2 is that the rail arrangement 18 is disposed outside of the patient access zone 16. This way, the rail arrangement 18 and at least a part of the support arrangement 16 can be kept outside of an operational zone or active zone near the object of interest. Furthermore, in another example, the rail arrangement 18 can be, if seen from a side view, arranged above a horizontal height of the patient support 12. This allows for freedom of move for staff and equipment in the patient access zone, because the rail arrangement and part of the support arrangement 16 require space only in room areas above the heads of medical staff.

Figure 3:
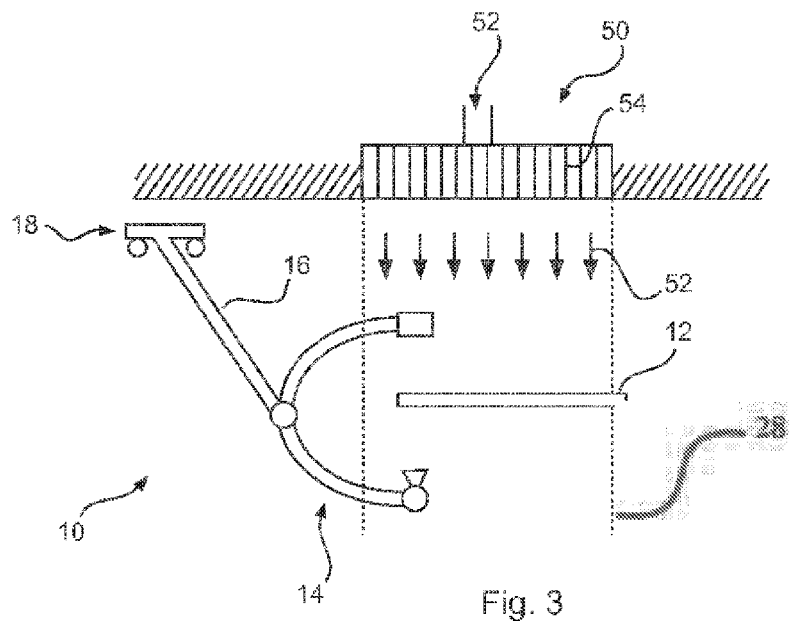
FIG. 3 schematically shows a further example of a medical imaging system from a side view with a laminar flow zone.

FIG. 3 shows a medical imaging system 10, comprising a further example of the rail arrangement 18, a support arrangement 16, and the image acquisition arrangement 14, which are connected to each other. The image acquisition arrangement 14 is shown as a C-arc structure, but can also be provided as any other support structure and shape. Furthermore, a laminar flow zone 28 is shown, which covers a part of a patient support 12. The laminar flow zone 28 is defined by a laminar flow of supply-air 52, which is provided by an external system (not shown). The supply-air 52 is usually pre-set-treated and filtered and is fed into an air supply arrangement 50, which comprises supply-air outlets 54, which generate an air-flow, for example in a laminar flow manner. The shown air supply arrangement including the supply-air outlets 54 can be seen as one option or possibility for generation of a laminar air-flow or down-flow. The laminar flow zone 28 should therefore be seen as independently from the air supply arrangement 50. The image acquisition arrangement can partly be located within the laminar flow zone 28 for acquisition of medical images. This can cause interference between the image acquisition arrangement and the laminar air-flow and cause turbulences, which are generally not desirable. A stand-by position of the image acquisition arrangement should therefore be outside of the laminar flow zone, or at least have minimal interference with the laminar air flow. In a parking position of the image acquisition arrangement 14, any equipment of the imaging system should be removed from the laminar flow zone 28.

In an example (not shown in detail), the image acquisition arrangement 14 can be moved into a position, in which the image acquisition arrangement 14 is not hindering or disturbing the work on and around the patient support, but in which the image acquisition arrangement 14 is still arranged in the flow such that the parts and areas of the image acquisition arrangement 14 that will be arranged near or above the patient will stay clean due to the clean air provided. Thus, the rail arrangement is provided outside the flow zone, while a part of the equipment is at least partly inside the flow zone.

The "keep-clean" position may be the stand-by position, or may be provided as a further position.

Figure 4:
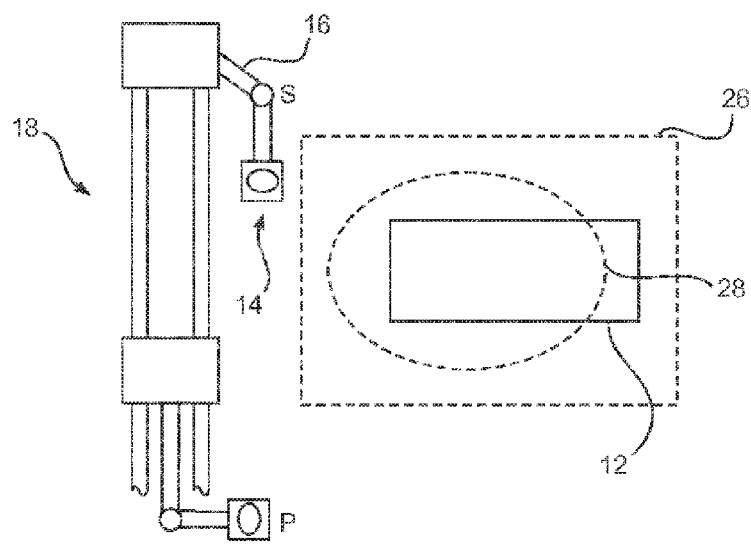
FIG. 4 schematically shows an example of a medical imaging system from a top view with a stand-by position and a parking position.

FIG. 4 shows an example of the medical imaging system 10 with the rail arrangement 18, the support arrangement 16, and the image acquisition arrangement 14. FIG. 4 further shows two separate possible positions of the support arrangement 16 and the image acquisition arrangement 14. An S-position describes a stand-by position, which is of advantage when the equipment is temporarily not needed and needs to stay in close distance to the object of interest to reduce time to reposition the image acquisition arrangement to acquire new images. In a P-position, the image acquisition arrangement 14 and the support arrangement 16 are arranged to free up or provide maximum space around the active or operational area and to move the imaging system out of way, if it is not needed. The patient support 12 is partly covered or surrounded by a laminar flow zone 28 and a patient access zone 26. In terms of the S-position (stand-by position), the image acquisition arrangement 14 is positioned outside of the patient access zone 26, however, it is possible that the image acquisition arrangement 14 partly locates within the laminar flow zone 28. The shown shape and size of the laminar flow zone 28 can vary and also extend the size of the patient access zone 26, or partly overlap each other. The shape of the laminar flow zone 28 and the patient access zone 26 can also vary, depending on room footprint, laminar flow generation methods and apparatus, shape and size of patient support 12, and others.

Figure 5:
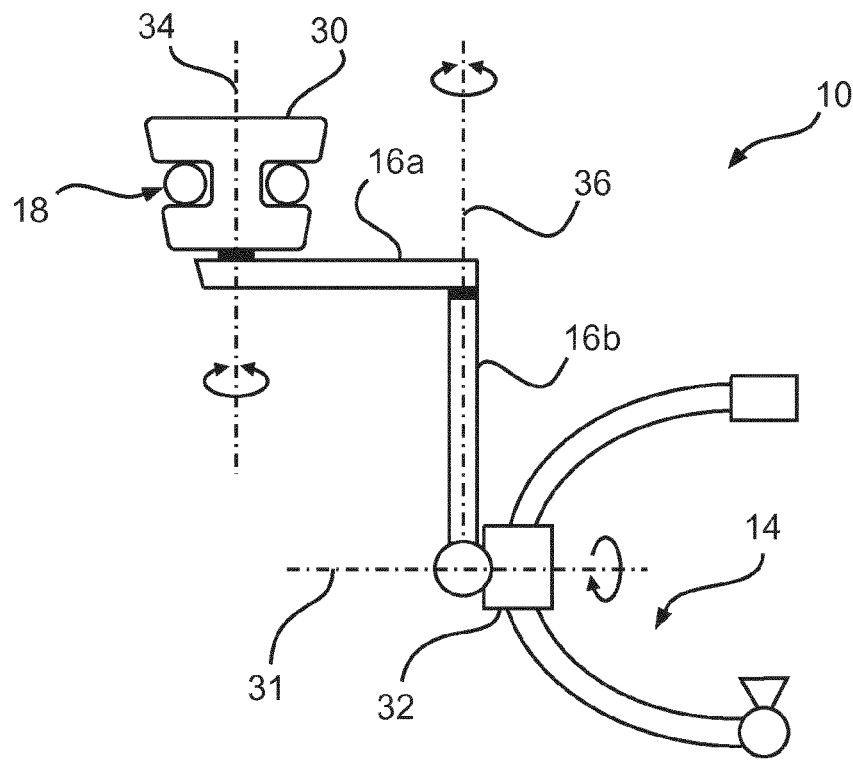
FIG. 5 schematically shows an example of a medical imaging system from a side view with two pivotable support arms.

FIG. 5 illustrates an example of the medical imaging system 10, comprising the rail arrangement 18, a first horizontal support arm 16a, a second vertical support arm 16b, and image acquisition connector 32. The support arm 16a is pivotally connected to a rail connector 30, which provides mechanical connection between the support arm 16a and the rail arrangement 18. The support arm 16a is pivotally movable around a vertical axis 34. The term vertical relates to a downwardly oriented direction which can deviate from the exact vertical arrangement. The support arm 16a extends horizontally; however, it can also extend in both vertical and horizontal direction. It should be noted, that the function of support arm 16a is to bridge a horizontal distance, therefore at least a certain degree of horizontal extension is necessary to provide a necessary offset or distance of the two pivotal axes 34 and 36. The rail connector 30 can slide along a longitudinal rail extension of the rail arrangement 18. The second support arm 16b is pivotally mounted around a vertical axis 36. Also here, a deviation from the exact vertical position of plus 30 degrees to minus 30 degrees can be possible, for example up to 60 degrees. In addition to the rotational movement, the support arm 16b can also move in all other directions in relation to the horizontal support arm 16a. The image acquisition connector 32 provides movement of the image acquisition arrangement around a horizontal axis 31, also known as "propeller movement". In another example, further pivotal movements of the image acquisition arrangement in relation to the second support arm 16b are possible in the three-dimensional directions. A horizontal axis refers to a mainly horizontal arrangement, which can allow deviations from an exact horizontal position of minus 30 degrees to plus 30 degrees.

Figure 6:
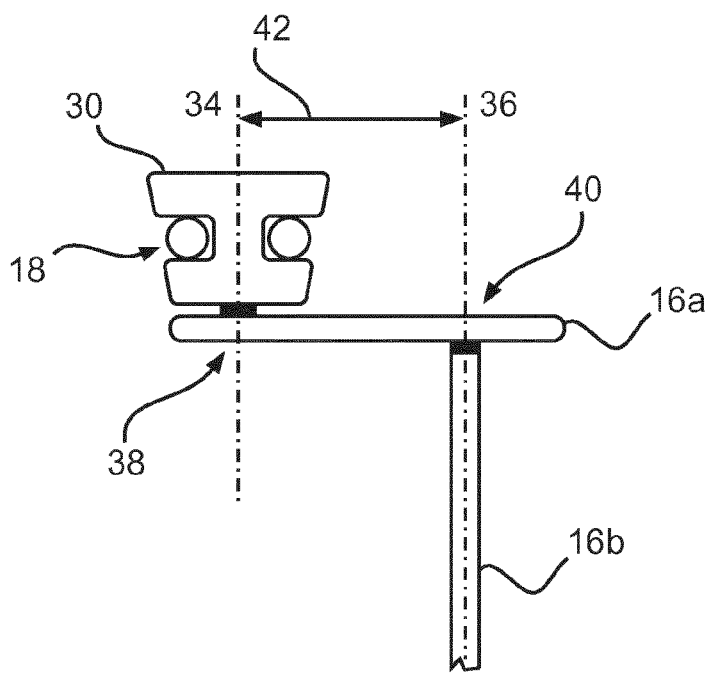
FIG. 6 schematically illustrates a rail arrangement, a rail connector, and two support arms as part of a medical imaging system in a further example.

FIG. 6 illustrates schematically an example of the rail arrangement 18, the rail connector 30, a mounting point 38 of the rail connector at the first horizontal support arm 16a, and a mounting point 40 of the second support arm 16b at the first support arm 16a. The first support arm 16a is pivotally mounted to the rail connector 30 around an axis 34. The second support arm 16b is pivotally mounted to the first support arm 16a around an axis 36. A horizontal distance 42 between the two axes 34 and 36 is adjustable. This can be achieved by moving the first mounting point 38 of the rail connector 30 along the extension of the first support arm 16a, and/or by changing or moving or displacing the mounting point 40 of the second support arm 16b along a length of the horizontal support arm 16a. By changing or adjusting this distance 42, a horizontal displacement or moving of the image acquisition arrangement can be achieved. Due to the transversal arrangement of the rail arrangement 18, it is provided to change the horizontal position of the image acquisition arrangement 14 to reach areas of the patient support 12 for image acquisition purposes. For example, a combination of an adjustment or change of the distance 42 and a rotation or pivoting around the axes 34 and 36 can provide the necessary flexibility to position the imaging system accordingly.

Figure 7:
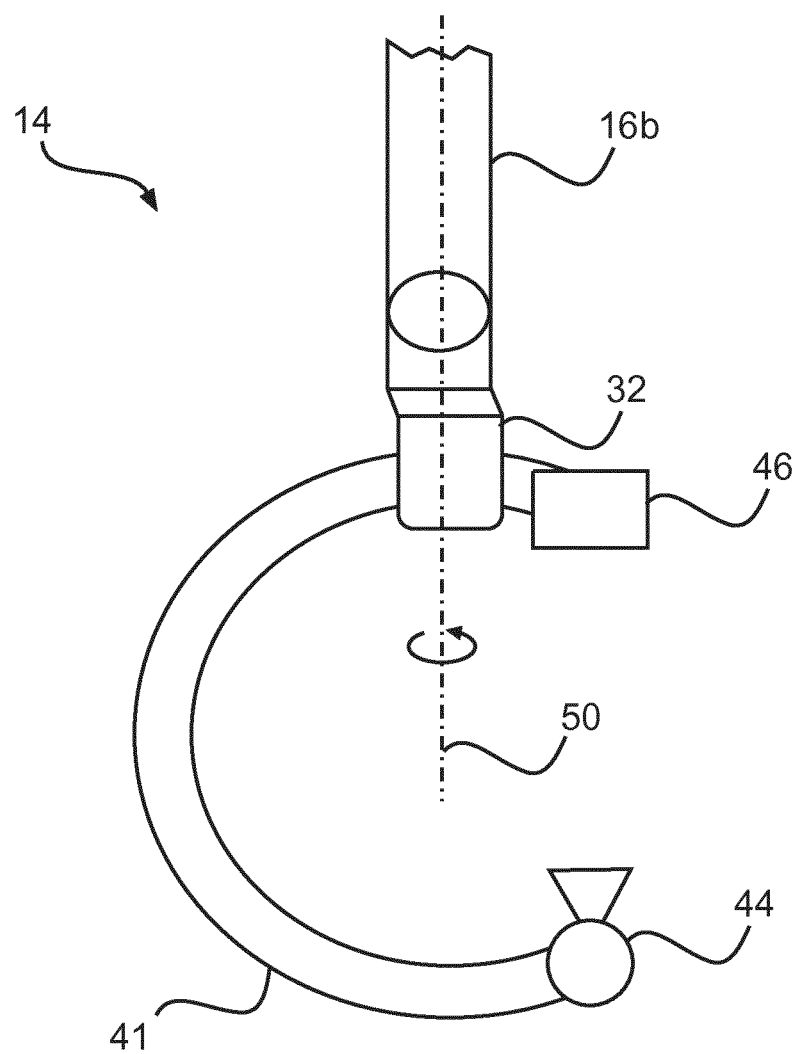
FIG. 7 schematically shows an example of an image acquisition arrangement and support arrangement with a mounting on top of a C-arm of a medical imaging system.

In FIG. 7, an alternative option is shown for mounting a support arm 16b to a top side of a C-arc 41 by means of an image acquisition connector 32. The C-arm 41 further comprises an X-ray source 44 and a detector 46, which is arranged opposite the X-ray source 44. The image acquisition connector 32 allows a pivoting movement of the C-arc around a vertical axis 50. In addition, the image acquisition connector 32 allows a sliding or gliding of the C-arc in radial direction, performing a roughly circular movement of the X-ray source 44/detector 46 arrangement.

It has to be noted that embodiments of the invention are described with reference to different embodiments. However, a person skilled in the art will gather from the above and the following description that, unless otherwise notified, any combination between features relating to different embodiments is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical X-ray imaging system, comprising:
a patient support;
an X-ray image acquisition arrangement comprising a C-arm having an X-ray source and an X-ray detector provided at opposing ends;
a support arrangement with a rail connector and an image acquisition connector and at least two support arms;
a rail arrangement;
wherein the image acquisition arrangement acquires image information of an object of interest arranged on the patient support;
wherein the rail arrangement is provided overhead;
wherein the support arrangement is movably mounted to the rail arrangement, wherein the support arrangement is movable at least along the rail arrangement;
wherein the rail connector couples the support arrangement to the rail arrangement;
wherein the image acquisition connector couples the image acquisition arrangement to the support arrangement; and
wherein the support arms are movably connected to each other linking the image acquisition connector to the rail connector;
wherein a first horizontal support arm is mounted to the rail connector at a first mounting point pivotally around a first downwardly oriented axis;
wherein a second vertical support arm is mounted to the first horizontal support arm at a second mounting point pivotally around a second downwardly oriented axis at a first end of the second vertical support arm;
wherein at least one of the first mounting point is movable along the first horizontal support arm to adjust a horizontal distance between the first mounting point and the second mounting point, and the second mounting point is movable along the first horizontal support arm to adjust a horizontal distance between the first mounting point and the second mounting point, wherein the image acquisition connector is mounted to a second end of the second vertical support arm, wherein the image acquisition arrangement is movable in relation to the second vertical support arm;

wherein the image acquisition arrangement is movably mounted to the support arrangement to allow image acquisition of the object from different directions;

wherein the patient support has a longitudinal direction; and wherein the rail arrangement extends in a longitudinal rail direction transversely to the longitudinal direction of the patient support.

2. Imaging system according to claim 1, wherein at least one of at least one rail mounts the first horizontal support arm is mounted to the rail connector at the first mounting point, and the at least one rail mounts the second vertical support arm is mounted to the first horizontal support arm at the second mounting point.

3. Imaging system according to claim 1, wherein the rail arrangement is disposed above and besides the patient support.

4. Imaging system according to claim 1,
wherein the patient support is at least partly surrounded by a predetermined patient access zone; and
wherein the rail arrangement is disposed above and outside of the patient access zone.

5. Imaging system according to claim 1,
wherein the patient support is at least partly located in a predetermined laminar flow zone; and
wherein the rail arrangement is disposed outside the laminar flow zone.

6. Imaging system according to claim 1, wherein the support arrangement is adapted to position the image acquisition arrangement at least in:
an operational position, in which the image acquisition arrangement acquires image information of the object of interest; and
a parking position, in which the image acquisition arrangement is provided outside a patient access zone and/or outside a laminar flow zone.

7. Imaging system according to claim 1, wherein the support arrangement allows the image acquisition arrangement to be positioned in a stand-by position, in which the image acquisition arrangement is outside of a patient access zone.

8. Imaging system according to claim 1, wherein the C-arm is movably mounted to the image acquisition connector; and
wherein the mounting of the C-arm is provided:
I) sidewise at an intermediate portion midway between the opposing ends of the C-arm;
wherein the image acquisition connector provides a pivoting movement of the C-arm around a horizontal axis; or
II) on top at the upper end of the two opposing ends; wherein the image acquisition connector provides a pivoting movement of the C-arm around a vertical axis.

9. Imaging system according to claim 1, further comprising:
an air supply arrangement providing treated supply-air;
wherein supply-air outlets are provided overhead supplying the supply-air in a laminar air-flow manner towards the patient support defining a laminar flow zone.

10. Imaging system according to claim 1, further comprising at least one of the group of:
movable lighting equipment;
movable display equipment; and
media rack;
wherein the lighting equipment and/or display equipment and/or media rack are mounted overhead outside a laminar air zone.

* * * * *